United States Patent [19]
Terhune et al.

[11] 3,936,410
[45] Feb. 3, 1976

[54] TRIARYL PHOSPHATE ESTER PLASTICIZERS FOR POLYVINYL CHLORIDE COMPOSITIONS

[75] Inventors: F. Lee Terhune, Westport, Conn.; Gordon A. Rampy, Nitro, W. Va.

[73] Assignee: FMC Corporation, Philadelphia, Pa.

[22] Filed: Sept. 23, 1974

[21] Appl. No.: 508,341

Related U.S. Application Data

[62] Division of Ser. No. 404,380, Oct. 9, 1973, Pat. No. 3,859,395.

[52] U.S. Cl................................................ 260/30.6 R
[51] Int. Cl.².......................... C08J 3/18; C08K 5/51

[58] Field of Search .............................. 260/30.6 R

[56] References Cited
UNITED STATES PATENTS

| | | | |
|---|---|---|---|
| 3,553,155 | 1/1971 | Garrett.......................... | 260/30.6 R |
| 3,576,923 | 4/1971 | Randell et al.................. | 260/30.6 R |
| 3,845,000 | 10/1974 | Pasley........................... | 260/30.6 R |

*Primary Examiner*—Allan Lieberman

[57] ABSTRACT

Composition and process for certain tris(isopropylphenyl) phosphate esters particularly suited for use as polyvinyl chloride plasticizers.

1 Claim, No Drawings

TRIARYL PHOSPHATE ESTER PLASTICIZERS FOR POLYVINYL CHLORIDE COMPOSITIONS

This is divisional application of application Ser. No. 404,380, filed Oct. 9, 1973, now U.S. Pat. No. 3,859,395, patented Jan. 7, 1975.

This invention relates to improved triaryl phosphate esters and methods for preparing same. More particularly, this invention relates to an improved form of a tris(isopropylphenyl) phosphate prepared from a propylated phenol reaction mixture and containing a high proportion of meta- and para-monoisopropylphenyl radicals.

Triaryl phosphate esters have been widely used as plasticizers for polyvinyl chloride resins. Compounds such as triphenyl phosphate, tricresyl phosphate, cresyl diphenyl phosphate and the like have been used for a number of years. Mixed triaryl phosphates such as mixed alkylphenyl/phenyl phosphates are also known and are disclosed, for example, in U.S. Pat. Nos. 3,553,155, issued Jan. 5, 1971, to Garrett; 3,071,549, issued Jan. 1, 1963, to Stark; and 3,576,923, issued Apr. 27, 1971, to Randell et al. However, it is always desirable to provide triaryl phosphates which exhibit an improved plasticizing effect and efficiency when formulated into polyvinyl chloride resin formulations.

In accordance with the present invention, there is provided a triaryl phosphate ester of the formula $(RO)_3PO$ wherein R represents radicals consisting essentially of:

a. at least 90% by weight monoisopropylphenyl radicals, with the proviso at least 80% by weight are a mixture of meta- and para-monoisopropylphenyl radicals, the mixture containing at least 50 to 90% by weight meta-isopropylphenyl radicals based on the weight of the mixture;

b. 0 to 5% by weight phenyl radicals; and c. 5 to 10% by weight of di-, or tri-isopropylphenyl radicals.

Thus, the novel triaryl phosphate esters of the present invention are characterized as having only a very small proportion of phenyl radicals and a very substantial proportion of meta- and para-monoisopropylphenyl radicals. Triaryl phosphate esters heretofore produced by the phosphorylation of alkylated, particularly propylated, phenol reaction mixtures have generally contained fairly substantial proportions of phenyl radicals in the final product. The prior art fails to recognize the advantage to be gained by minimizing the presence of phenyl radicals and maximizing the presence of meta- or para-monoisopropylphenyl radicals in certain relative proportions to each other.

Nevertheless, it has been found that the novel triaryl phosphate esters of the present invention function as excellent plasticizers and are a significant improvement in that they provide a combination of properties not found in conventional triaryl phosphate esters. The novel phosphate esters of the present invention have a plasticizer efficiency which compares favorably to the lower molecular weight triaryl phosphates, and, importantly, this efficiency is retained after exposure to high temperatures. They have an extremely low volatility; they have excellent flame-retardant characteristics considering the molecular weight and the high proportion of isopropyl groups present; they have a low viscosity, and the heat and light stability of polyvinyl chloride compositions containing the novel triaryl phosphates is excellent. A surprising and advantageous property is that the phosphate plasticizers of the present invention are substantially non-migrating when formulated in polyvinyl chloride compositions. Migration of phosphate plasticizers onto lacquered, varnished or other polymeric surfaces has restricted their utility in some applications.

Moreover, when employed in plastisol formulations, the triaryl phosphates of the present invention markedly improve the viscosity stability, and such formulations exhibit a gel time of about two hours at 65°C. This effect is a major improvement over heretofore used phosphate plasticizers for plastisols. It should be also noted that the novel triaryl phosphates of the present invention are also suitable for use as hydraulic fluids, and in this connection they exhibit improved hydrolytic stability and improved compression ignition properties.

The novel triaryl phosphates of the present invention are preferably prepared directly from the reaction mixture produced by partially propylating phenol. Generally, the process involves the propylation of phenol, the isomerization of the propylate and the phosphorylation of a certain distillate fraction obtained from the isomerized propylate.

The propylation is carried out by the Friedel-Crafts reaction using about 10 to 40% by weight of propylating agent, based on the weight of phenol, and preferably about 20–25% by weight propylating agent is employed. The reaction is carried out preferably with propylene, but 2-propyl chloride or 2-propanol may also be used in accordance with known techniques, as disclosed, for example, in U.S. Pat. No. 3,576,923. The propylation is carried out generally between about 130° and 150°C and preferably at about 140°C. Conventional Friedel-Crafts catalysts may be used. Exemplary are Lewis acids such as aluminum chloride, ferric chloride, stannous chloride, zinc chloride, boron trifluoride, titanium tetrachloride, as well as Bronsted acids as exemplified by sulfuric acid, orthophosphoric acid, p-toluene sulfonic acid, perchloric acid, acid treated Montmorillonite clay and other activated clays and earths.

After the propylation is concluded, the propylated phenol reaction mixture is isomerized by heating and stirring in the presence of a small amount of Lewis or Bronsted acid catalyst. The same catalysts suitable for the alkylation step are suitable in the isomerization step. Preferably, acid treated Montmorillonite clay is used in amount between about 1 to 5% by weight, based on the weight of the reaction mixture, at a temperature of about 160°–200°C, preferably about 180°C, for several hours in order to effect isomerization and produce an alkylate having a high proportion of monoisopropyl radicals located in the meta- and para-positions.

The isomerized alkylate is then fractionally distilled and only fractions boiling between about 220°C and 235°C are collected and combined. The combined fractions are then phosphorylated in a conventional manner. The preferred phosphorylation catalyst is aluminum chloride, but other Lewis acid catalysts are suitable. The preferred phosphorylating agent is phosphorus oxychloride, but phosphorus oxybromide or phosphoric acid may also be employed. The phosphorylation reaction employs from about 0.05 to 1.5%, preferably 1%, by weight of phosphorylation catalyst and about 2.5 to 3.5 moles of propylated phenol per mole of phosphorylating agent. The reaction is carried out at a temperature between about 100°–200°C, and preferably by slow addition of the phosphorylating agent at a temperature of 100°–110°C and thereafter increasing the temperature to about 180°–190°C to complete the reaction. The phosphate ester product is recovered by distilling to obtain a distillate having a boiling point range of 265°–275°C (4mm/Hg) and the distillation is washed with an aqueous alkaline solution and water, and treated with activated carbon and clay and thereafter filtered.

In the final product, the distribution of isopropylphenol and phenyl radicals will be such that there are present at least 90% ortho-, meta- and para-monoisopropylphenyl radicals and at least 80%, and preferably at least 85%, by weight are mixed meta- and para-monoisopropylphenyl radicals. There are present 5-10% di- or tri-isopropylphenyl radicals. Less than 5%, and preferably less than 1% are phenyl radicals. Most preferably, no analyzable (i.e., only traces of) phenyl radicals are present.

The final product contains at least 80% of a mixture of monoisopropylphenyl radicals located in the meta- and para- positions. Of these meta- and para-isopropylphenyl radicals, at least 50–90% by weight should be meta-isopropylphenyl radicals and 50 to 10% are para-isopropylphenyl radicals. The preferred distribution in this mixture is 65 to 75% of meta-isopropylphenyl radicals and 35 to 25% of para-isopropylphenyl radicals.

Considering the relatively high molecular weight of the phosphate ester product produced according to the present invention, it has a number of highly desirable properties when formulated into polyvinyl chloride compositions. The plasticizer efficiency is unusually good and the retention of efficiency (modulus and elongation) after exposure to high temperatures is a substantial improvement over most heretofore used phosphate plasticizers. The plasticized product has a very low volatility which is an important property for many plasticizer applications, such as in vinyl upholstery for use in automobiles. These properties are indicative of improved permanence. Again, considering the presence of a relatively large number of isopropyl groups, plasticized polyvinyl chloride compositions containing the novel product of the present invention, exhibit excellent flame-retardant and improved smoke-suppressant qualities.

The novel triaryl phosphate plasticizers of the present invention exhibit an unusual property in that they are substantially non-migrating plasticizers. When plasticized polyvinyl chloride compositions are placed into contact with other polymeric materials, such as cellulose nitrate or acrylic lacquers, migration of the plasticizer onto these surfaces may occur. Thus, when plasticized polyvinyl chloride articles contact surfaces containing a polymeric coating compatible with the plasticizer, such as lacquered automobile or furniture surfaces, the migration phenomenon can soften or destroy the surface finish. Migration onto an adhesive surface can weaken the adhesive bond; rigid polymers can become brittle and cracked as the result of plasticizer migration. It has been generally recognized that phosphate plasticizers generally exhibited a more pronounced tendency toward migration, particularly onto lacquered surfaces, when formulated into polyvinyl chloride compositions. The triaryl phosphate plasticizers of the present invention have been found to exhibit little or no migration and therefore offer an advantage not available in heretofore employed triaryl phosphate plasticizers. Thus, they are particularly suitable for use in connection with polyvinyl chloride coverings for electrical and telephone wires which frequently come into contact with surfaces which can be adversely affected by plasticizer migration.

Plastisol formulations containing the novel triaryl phosphates produced in accordance with the present invention are a particularly preferred embodiment. Plastisols are dispersions of finely divided "dispersion grade" polyvinyl chloride resin in a plasticizer. It has been found that plastisol formulations made with the novel products of the present invention exhibit a marked improvement with regard to viscosity stability and at the same time have a desirable rapid cure rate. Thus, standard plastisol formulations (88 phr plasticizer) containing the novel products of the present invention exhibit gel times at 65°C of about two hours or more. Polyvinyl chloride plastisols containing heretofore known phosphate plasticizers have exhibited gel times in the range of about 5 to 30 minutes at 65°C. Longer gel times, which are a distinct advantage, have generally been possible only with compositions containing phthalate or adipate plasticizer which lack the desirable flame-retardant qualities of phosphates. Plastisols formulated in accordance with the present invention will generally contain from about 30 to 150, preferably 50 to 100, parts of plasticizer per 100 parts of polyvinyl chloride resin.

The novel phosphate ester plasticizers of the present invention are employed in conventional quantities in polyvinyl chloride compositions, that is, about 5–150 parts by weight of plasticizer per 100 parts of vinyl chloride polymer.

The invention is further illustrated by the following examples which are not to be considered as limitative of its scope. Parts and percentages are by weight and temperatures are in degrees centigrade unless otherwise indicated.

EXAMPLE I 1000 parts of phenol was propylated with 21% by weight propylene at a temperature of 140°C using 75 parts of an activated Montmorillonite clay catalyst.

A 2300 ml portion of the propylate was isomerized by heating with stirring at 180°C for 23 hours in the presence of 46 grams of activated Montmorillonite clay catalyst. Percent by weight analysis of the propylate both before and after isomerization is shown below.

|  | Before Isomerization | After Isomerization |
|---|---|---|
| Phenol | 38.0 | 37.7 |
| Ortho - IPP* | 34.9 | 9.9 |
| Meta & Para - IPP | 13.7 | 42.0 |
| 2,6 - DIPP* | 4.0 | 0.1 |
| 2,4 - DIPP | 7.3 | 2.4 |
| 2,5 & 3,5 - DIPP | 0.6 | 7.8 |
| 2,4,6 - TIPP* | 1.4 | 0.1 |
| 2,4,5 - TIPP | 0.1 | 0.0 |

*IPP, DIPP and TIPP represent, respectively, mono-, di- and tri-isopropyl phenol.

The isomerized alkylate was fractionally distilled at atmospheric pressure and separated into fractions having analyses shown below.

| Fraction No. | b.p. °C | g | Composition, wt. % | | | |
|---|---|---|---|---|---|---|
| | | | Phenol | o-TPP | m&p-IPP | Other |
| 1 | 100-190 | 585 | 91 | 5 | 4 | 0 |
| 2 | 190-215 | 266 | 77 | 11 | 13 | 0 |
| 3 | 215-220 | 290 | 42 | 22 | 36 | 0 |
| 4 | 220-227 | 319 | 0 | 20 | 78 | 2 |
| 5 | 228-232 | 322 | 0 | 6 | 88 | 6 |
| 6 | 232 | 86 | 0 | 1 | 80 | 21 |
| Residue | — | 195 | 0 | 0 | 10 | 90 |

600 grams of the combined fractions 4, 5 and 6 were phosphorylated in the presence of 6 grams of $AlCl_3$ by adding 210 grams of $POCl_3$ over a period of 2 hours at 110°C. The temperature was then slowly raised to 180°C over a period of one hour and held at 180°C for an additional 2½ hours. To complete the reaction, 18 more grams of alkylate were added and the temperature was raised to 190°C and maintained at this temperature for 3 more hours.

The 681 grams of crude phosphorylation batch was distilled through a packed column (diameter of 4 inches) at 4 mm. Hg and 265°-275° C to give 590 grams of product. The product was washed successively with equal volumes of 2% NaOH solution and water three times at 80°C. The washed product was heated to 120°C with 0.5% activated carbon and 0.5% filter clay and then filtered under vacuum with filter aid. The product has the following properties:

| | |
|---|---|
| Sp. gr. at 20/20°C | 1.090 |
| Color, Pt-Co (ASTM D-1209-C2) | 60 |
| Acidity, % as Acetic Acid (ASTM D-1613-61-T) | 0.001 |
| Viscosity, cs at 100°F | 45.2 |
| Free Phenol, % (ASTM D58-20) | 0.05 |

The product was saponified and by analyzing (vapor phase chromatograph) the recovered phenols the product was found to have the following composition:

| | Weight Percent |
|---|---|
| Phenol | 0.0 |
| Ortho-IPP | 7.7 |
| Meta*- & Para*- IPP | 85.8 |
| 2,6 - DIPP | 0.0 |
| 2,4 - DIPP | 3.5 |
| 2,5 & 3,5 - DIPP | 3.0 |
| 2,4,6 - TIPP | 0.0 |
| 2,4,5 - TIPP | 0.0 |
| | 100.0-Total |

*70% meta- isomer, 30% para- isomer.

EXAMPLE II

Milled plasticized polyvinyl chloride compositions were prepared using 60 parts of the phosphate esters listed below, 100 parts of "GEON 101 EP" as the general purpose vinyl chloride polymer and 1.5 parts of "Ferro 75-001" barium-cadmium stabilizer. The evaluations of the compositions are set forth below in Table I. Comparison A is cresyl diphenyl phosphate. Comparison B is an isopropylphenyl phosphate prepared by phosphorylating the alkylate of Example I before isomerization, the phosphorylation being carried out in the same manner as described in Example I. Comparison C is tricresyl phosphate.

Table 1

| Test Method | Phosphate Ester Plasticizer | | | |
|---|---|---|---|---|
| | Comp. A | Comp. B | Comp. C | Prod. of Ex. 1 |
| Plasticizer Efficiency-ASTM D 416 2T | | | | |
| 100% Modulus (psi) | 1475 | 1727 | 1528 | 1846 |
| 100% Modulus (psi) Aged 7 days at 100°C | 2425 | 2531 | 1915 | 1908 |
| Ultimate Tensile Strength (psi) | 2992 | 2909 | 2893 | 2807 |
| Ultimate Elongation (%) | 318 | 318 | 290 | 324 |
| Shore Durometer A Hardness | 75 | 79 | 72 | 79 |
| % Loss, Carbon Volatility ASTM D1203-61T | 0.80 | 0.64 | 0.35 | 0.18 |
| Flame Retardance-ASTM D-2843 | | | | |
| Oxygen Index | 29.6 | 29.6 | 29.9 | 28.6 |
| Smoke, Max Density (%) | 97 | 95 | 96 | 93 |
| Smoke Density Rating (10 mi.) | 82.3 | 79.2 | 79.8 | 76.5 |
| Migration, lacquer mar - ASTM D 2134 66 (% Softening) | | | | |
| Sward Rocker, 24 hours at 75°C | 53 | 19.4 | 33.2 | 0 |
| Heat Stability*-Color 50 (mins.) | 17 | 22 | 19 | 25 |
| -Color 500 (mins.) | 25 | 31 | 27 | 34 |

*Samples ½" × 1" × 0.075" thick placed on aluminum plate in forced draft oven at 177°C and a sample removed at regular intervals. Time is noted when samples reach A.P.H.A. Pt-Co color number of 50 and 500.

EXAMPLE III

Comparative properties of these phosphate esters are listed below in Table 2:

Table 2

| | Phosphate Ester Properties | | |
|---|---|---|---|
| | Comp. A* | Comp. B* | Prod. of Ex. 1 |
| Flash Point, °F | 470 | 470 | 520 |
| Fire Point, °F | 550 | 550 | 630 |
| Pour Point, °F | −30 | −15 | −20 |
| Boiling Range at 4 mm Hg, °C | 235-255 | 220-270 | 265-275 |
| Vapor Pressure at 150°C | <.02 | <.02 | <.02 |
| Vapor Pressure at 200°C | 0.70 | 0.60 | .05 |

*Same as Example II.

EXAMPLE IV

Using a dispersion grade polyvinyl chloride resin, standard plastisol compositions were prepared (88 phr of plasticizer, 1.5 phr barium-cadmium stabilizer.) Gel times are listed in Table 3 below. It is significant that plastisols prepared with the product of this invention exhibit a marked improvement in viscosity stability as indicated by the gel time. A General Electric gel timer was used and the time required to form a thick semi-gel at 65°C is measured and recorded in minutes.

Table 3 -Plastisol Data

| Plasticizer | Gel Time(65°C) |
|---|---|
| Product of Example 1 | >120 minutes |
| Comparison B* | 27 minutes |
| Comparison C* | 8 minutes |

Table 3 -Plastisol Data-continued

| Plasticizer | Gel Time(65°C) |
|---|---|
| Comparison A* | 5 minutes |

*Same plasticizers as used in Example II.

What is claimed is:

1. A plasticized polyvinyl chloride composition containing 5 to 150 parts by weight of plasticizer per 100 parts of vinyl chloride polymer, wherein said plasticizer is a triaryl phosphate ester of the formula $(RO)_3PO$ wherein R represents radicals consisting essentially of:

a. at least 90% by weight monoisopropylphenyl radicals with the proviso that at least 80% by weight are a mixture of meta- and para- monoisopropylphenyl radicals, said mixture containing at least 50 to 90% by weight meta-isopropylphenyl radicals, based on the weight of said mixture;

b. 0 to 5% by weight phenyl radicals; and c. 5 to 10% by weight di- or tri-isopropylphenyl radicals.

* * * * *

UNITED STATES PATENT OFFICE
CERTIFICATE OF CORRECTION

PATENT NO. : 3,936,410
DATED : February 3, 1976
INVENTOR(S) : F. LEE TERHUNE and GORDON A. RAMPY It is certified that error appears in the above-identified patent and that said Letters Patent are hereby corrected as shown below:

Column 3, line 38 "volality" should read --volatility--.

Column 5, line 5, Table heading "O-TPP" should read --O-IPP--.

Signed and Sealed this

Sixteenth Day of November 1976

[SEAL]

Attest:

RUTH C. MASON
Attesting Officer

C. MARSHALL DANN
Commissioner of Patents and Trademarks